(12) United States Patent  
Naftali et al.

(10) Patent No.: US 7,924,419 B2  
(45) Date of Patent: Apr. 12, 2011

(54) ILLUMINATION SYSTEM FOR OPTICAL INSPECTION

(75) Inventors: Ron Naftali, Shoham (IL); Avishay Guetta, Rehovot (IL); Haim Feldman, Nof-Aylon (IL); Doron Shoham, Rehovot (IL)

(73) Assignees: Applied Materials Israel, Ltd., Rehovot (IL); Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 12/626,592

(22) Filed: Nov. 25, 2009

(65) Prior Publication Data

US 2010/0097680 A1  Apr. 22, 2010

Related U.S. Application Data

(60) Division of application No. 11/394,218, filed on Jan. 23, 2006, now Pat. No. 7,630,069, which is a continuation of application No. 10/511,085, filed as application No. PCT/US03/28054 on Sep. 8, 2003, now abandoned.

(60) Provisional application No. 60/415,082, filed on Sep. 30, 2002.

(51) Int. Cl.  
*G01N 21/00* (2006.01)

(52) U.S. Cl. .................. 356/237.2; 356/237.1

(58) Field of Classification Search ..... 356/237.1–237.5  
See application file for complete search history.

(56) References Cited

U.S. PATENT DOCUMENTS

| | | |
|---|---|---|
| 3,628,080 A | 12/1971 | Lindequist |
| 3,967,123 A | 6/1976 | Deylius et al. |
| 4,619,508 A | 10/1986 | Shibuya et al. |
| 4,933,961 A | 6/1990 | Rushbrooke et al. |
| 5,161,008 A | 11/1992 | Funk |
| 5,228,101 A | 7/1993 | Lebby et al. |
| 5,264,912 A | 11/1993 | Neukermans et al. |
| 5,359,447 A | 10/1994 | Hahn et al. |
| 5,420,954 A | 5/1995 | Swirhun et al. |
| 5,500,770 A | 3/1996 | Zinter et al. |
| 5,526,458 A | 6/1996 | Hochgraf |
| 5,574,276 A | 11/1996 | Ishimaru |
| 5,633,721 A | 5/1997 | Mizutani |
| 5,633,747 A | 5/1997 | Nikoonahad |
| 5,650,614 A | 7/1997 | Yatsutake et al. |
| 5,673,144 A | 9/1997 | Chastang et al. |
| 5,729,374 A | 3/1998 | Tiszauer et al. |

(Continued)

FOREIGN PATENT DOCUMENTS

CA  2366566 A1  10/2000

(Continued)

OTHER PUBLICATIONS

European Patent Office, Communication pursuant to Article 94(3) EPC, issued for EP 03799277.3-1234 on Feb. 17, 2009.  
Japanese Patent Office, Notice of Reasons for Rejection, issued for patent application P2004-541515 on Aug. 12, 2008, with English translation.  
Japanese Patent Office, Notice of Reasons for Rejection, issued for patent application P2004-541515 on Feb. 17, 2009, with English translation.

(Continued)

*Primary Examiner* — Michael P Stafira  
(74) *Attorney, Agent, or Firm* — SNR Denton US LLP

(57) ABSTRACT

Apparatus for generating optical radiation includes a laser, which is configured to operate in multiple transverse modes simultaneously so as to generate an input beam, which is characterized by a first speckle contrast. The transverse modes of the input beam are optically mixed so as to generate an output beam have a second speckle contrast, which is substantially less than the first speckle contrast.

6 Claims, 10 Drawing Sheets

U.S. PATENT DOCUMENTS

| | | | |
|---|---|---|---|
| 5,729,383 | A | 3/1998 | Chastang et al. |
| 5,739,542 | A | 4/1998 | Sudo et al. |
| 5,774,224 | A | 6/1998 | Kerstens |
| 5,801,824 | A | 9/1998 | Henley |
| 5,822,055 | A | 10/1998 | Tsai et al. |
| 5,900,941 | A | 5/1999 | Matsuyama et al. |
| 5,903,342 | A | 5/1999 | Yatsugake et al. |
| 5,933,473 | A | 8/1999 | Kitaguchi |
| 6,104,481 | A | 8/2000 | Isozaki et al. |
| 6,122,046 | A | 9/2000 | Almogy |
| 6,137,570 | A | 10/2000 | Chuang et al. |
| 6,249,381 | B1 | 6/2001 | Suganuma |
| 6,304,373 | B1 | 10/2001 | Zavislan |
| 6,313,465 | B1 | 11/2001 | Nittoh et al. |
| 6,323,984 | B1 | 11/2001 | Trisnadi |
| 6,347,173 | B1 | 2/2002 | Suganuma et al. |
| 6,369,888 | B1 | 4/2002 | Karpol et al. |
| 6,370,219 | B1 | 4/2002 | Peale |
| 6,388,744 | B1 | 5/2002 | Kubota |
| 6,429,931 | B1 | 8/2002 | Karpol et al. |
| 6,445,487 | B1 | 9/2002 | Roddy et al. |
| 6,522,437 | B2 | 2/2003 | Presley et al. |
| 6,556,290 | B2 | 4/2003 | Maeda et al. |
| 6,594,076 | B2 | 7/2003 | Satou |
| 6,621,570 | B1 | 9/2003 | Danko |
| 6,646,272 | B2 | 11/2003 | Rushbrooke et al. |
| 6,693,930 | B1 | 2/2004 | Chuang et al. |
| 6,778,267 | B2 | 8/2004 | Drake |
| 6,853,446 | B1 | 2/2005 | Almogy et al. |
| 6,895,149 | B1 | 5/2005 | Jacob et al. |
| 6,956,878 | B1 | 10/2005 | Trisnadi |
| 7,015,452 | B2 | 3/2006 | Benz et al. |
| 7,116,413 | B2 | 10/2006 | Vaez-Iravani |
| 7,136,159 | B2 * | 11/2006 | Tsai et al. ............ 356/237.5 |
| 2001/0030296 | A1 * | 10/2001 | Ishimaru et al. |
| 2001/0052975 | A1 * | 12/2001 | Biellak et al. |
| 2002/0067478 | A1 * | 6/2002 | Karpol et al. |
| 2003/0011850 | A1 * | 1/2003 | Sidorovich et al. |
| 2004/0008399 | A1 * | 1/2004 | Trisnadi |
| 2005/0219518 | A1 * | 10/2005 | Korngut et al. |

FOREIGN PATENT DOCUMENTS

| | | | |
|---|---|---|---|
| DE | 4 434 699 A1 * | 4/1996 | |
| EP | 0 589 179 A1 * | 3/1994 | |
| GB | 2 126 716 A * | 3/1984 | |
| JP | 62-235510 A | 10/1987 | |
| JP | 63-255917 A * | 10/1988 | |
| JP | 02-035447 A * | 2/1990 | |
| JP | 07-270328 | 10/1995 | |
| JP | 09-305094 A * | 11/1997 | |
| JP | 10-335240 A * | 12/1998 | |
| JP | 11-223795 A1 | 8/1999 | |
| JP | 2000-111832 A | 4/2000 | |
| JP | 2000-275182 | 10/2000 | |
| JP | 2001-250760 A * | 9/2001 | |
| JP | 2002-39960 | 6/2002 | |
| WO | 00/03234 A * | 1/2000 | |
| WO | 03/001186 A | 1/2003 | |
| WO | 03/027644 A1 | 4/2003 | |

OTHER PUBLICATIONS

Patent Cooperation Treaty, International Search Report for PCT/US03/28054, mailed Nov. 16, 2005, ISA: European Patent Office, Rijswijk, Netherlands.

Patent Cooperation Treaty, International Search Report for PCT/US03/28062, mailed Dec. 30, 2003, ISA: European Patent Office, Rijswijk, Netherlands.

Patent Cooperation Treaty, International Search Report for PCT/US03/28061, mailed Dec. 16, 2003, ISA: European Patent Office, Rijswijk, Netherlands.

European Patent Office, Communication pursuant to Article 96(2) EPC, issued for EP 03799276.5 on Oct. 11, 2006.

The State Intellectual Property Office of the Peoples Republic of China, First Office Action Notification, issued for patent application 038230976 on Dec. 22, 2006, with English translation.

The State Intellectual Property Office of the Peoples Republic of China, Second Office Action Notification, issued for patent application 038230976 on May 25, 2007, with English translation.

The State Intellectual Property Office of the Peoples Republic of China, Fourth Office Action Notification, issued for patent application 038230976 on Jun. 6, 2008, with English translation.

The State Intellectual Property Office of the Peoples Republic of China, Decision on Rejection, issued for patent application 038230976 on Oct. 10, 2008, with English translation.

The State Intellectual Property Office of the Peoples Republic of China, Notice of Reexamination, issued for patent application 038230976 on Nov. 4, 2009, with English translation.

Japanese Patent Office, Notice of Reasons for Rejection, issued for patent application P2004-541513 on Feb. 9, 2010, English translation.

Japanese Patent Office, Notice for Reasons of Rejection, issued for patent application P2004-541513 on Sep. 14, 2010, English translation.

Israel Patent Office, Official Action, issued for patent application 167,347 on Sep. 20, 2010, English Translation.

Zilko, J. L., AT&T OETC Quarterly Technical Report for Oct.-Dec. 1992, (Jan. 8, 1993).

Banwell, T. C. et al., VCSE laser transmitters for parallel data links, IEEE Journal of Quantum Electronics, vol. 29, No. 2, pp. 635-644 (Feb. 1993).

Chang-Hasnain, C. J. et al., Transverse Mode Characteristics of Vertical Cavity Surface Emitting Lasers, Appl. Phys. Lett., vol. 57, No. 3, pp. 218-220 (Jul. 1990).

Chang-Hasnain. C. J. et al., Dynamic, polarization, and transverse mode characteristics of vertical cavity surface emitting lasers, IEEE Journal of Quantum Electronics, vol. 27, No. 6, pp. 1402-1409 (Jun. 1991).

Jewell, J. L. et al., Vertical-cavity surface-emitting lasers: Design, growth, fabrication, characterization, IEEE Journal of Quantum Electronics, vol. 27, No. 6, pp. 1332-1346 (Jun. 1991).

Choa et al., High-speed Modulation of Vertical-Cavity Surface-Emitting Lasers, IEEE Photonics Technology Letters, vol. 3, No. 8, (Aug. 1991).

von Lehmen, A. C. et al., High speed operation of hybrid CMOS vertical cavity surface emitting laser array, Electronics Letters, vol. 27, No. 13, pp. 1189-1191, (Jun. 20, 1991).

Young, D. B. et al., Enhanced Performance of Offset-Gain High-Barrier Vertical-Cavity Surface-Emitting Lasers, IEEE Journal of Quantum Electronics, vol. 29, No. 6 (Jun. 1993).

Peters, M.G. et al., High-power vertical-cavity surface-emitting lasers efficiently coupled to optical fibers, OFC/IOOC'93 Technical Digest, WH2, pp. 110-111 (Feb. 21, 1993).

Geels, R.S. et al., Efficient vertical-cavity surface-emitting lasers with useful outputs to over 100° C, OFC'92 Technical Digest, WB3, pp. 102 (1992).

Geels, R. S., Vertical-Cavity Surface-Emitting Lasers: Design, Fabrication and Characterization, Ph.D. Dissertation, University of California Santa Barbara (Sep. 1991).

Peters et al., Vertical cavity surface emitting laser technology, Processing and packaging of semiconductor lasers and optoelectronic devices; Proceedings of the Meeting, Los Angeles, CA, Jan. 20-21, 1993 Society of Photo-Optical Instrumentation Engineers (SPIE Proceedings. vol. 1851).

Banwell, T. C. et al., 622 Mb/s Operation of Hybrid CMOS—Vertical Cavity Surface Emitting Laser Array, pp. 577-578 (1991).

Orenstein, M. et al, Apl. Phys. Lett. 56 (24), pp. 2384-2386 (Jun. 11, 1990).

Epworth, R.E., The phenomenon of modal noise in analogue and digital optical fiber system, 4th ECOC, Tech. Digest, pp. 492-501 (1978).

Dandliker, R., Berthold, A., and Maystre, F., How modal noise in multimode fibers depends on source spectrum and fiber dispersion, J. Lightwave Technol., 1985, LT-3, pp. 7-12.

Koonen, A., Bit-error-rate degradation in a multimode fiber optic transmission link due to modal noise, IEEE J. Sel. Areas Commun., 1986, SAC-4, pp. 1515-1522.

* cited by examiner

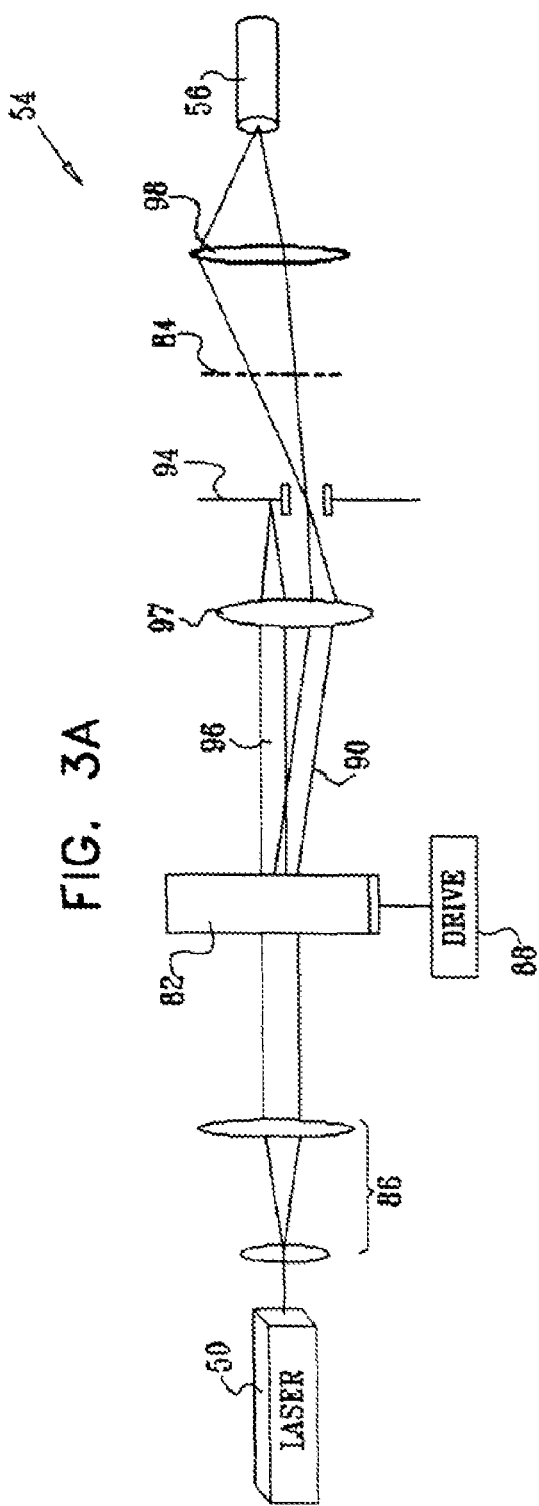
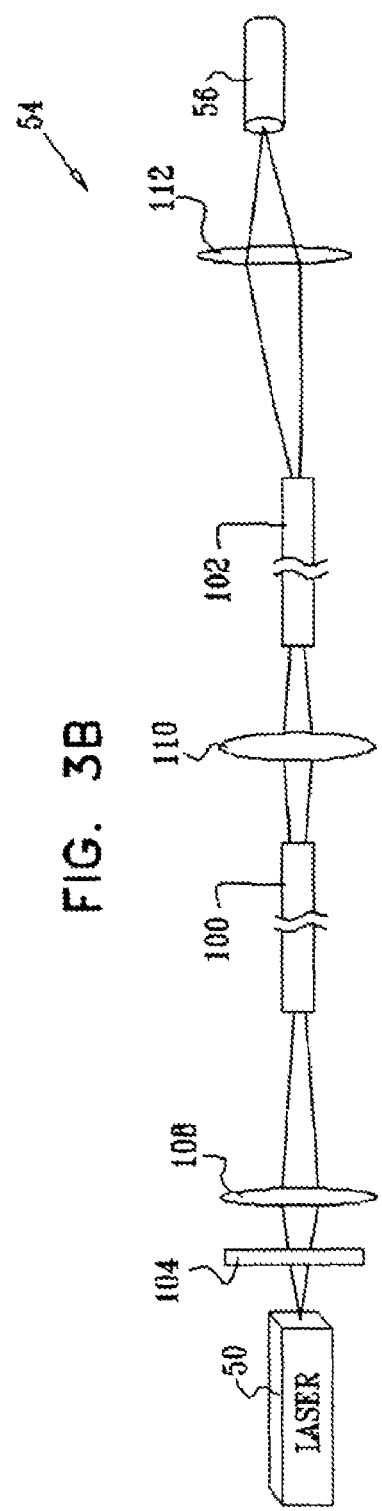

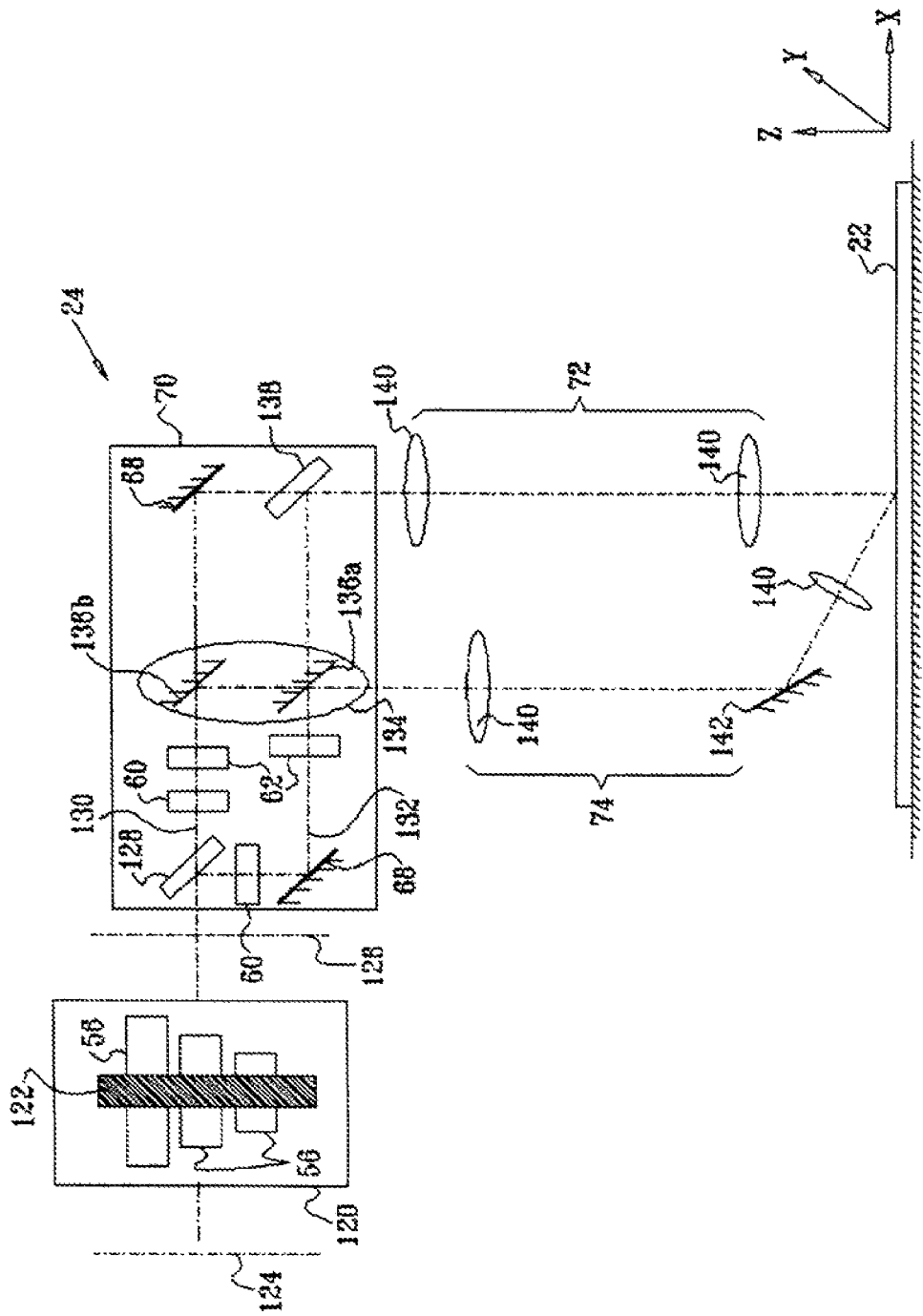

ILLUMINATION SYSTEM FOR OPTICAL INSPECTION

CROSS-REFERENCE TO RELATED APPLICATIONS

This application is a Divisional Application of U.S. patent application Ser. No. 11/394,218filed on Jan. 23, 2006, now U.S. Pat. No. 7,630,069, which is a Continuation and claims priority to U.S. patent application Ser. No. 10/511,085, entitled "Illumination system for optical inspection," filed on Oct. 14, 2004 now abandoned, which is a National Stage Entry and claims priority to PCT/US2003/028054, entitled "Illumination system for optical inspection," filed on Sep. 8, 2003, which is a non-provisional of and claims priority to Provisional Application No. 60/415,082, entitled "Dark field inspection system for defect detection on semiconductor wafers," filed on Sep. 30, 2002. This application is related to two other U.S. patent applications, U.S. patent application Ser. No. 10/511,092, entitled "Dark Field Inspection System", filed on Oct. 14, 2004, which is a National Stage Entry and claims priority to PCT/US2003/028062, entitled "Dark Field Inspection System," filed on Sep. 8, 2003, which claims priority to Provisional Application No. 60/415,082, and U.S. patent application Ser. No. 10/511,084, entitled "Inspection System with Oblique Viewing Angle", filed on Oct. 14, 2004, which is a National Stage Entry and claims priority to PCT/US2003/28061, entitled "Inspection System with Oblique Viewing Angle," filed on Sep. 8, 2003, which claims priority to Provisional Application No. 60/415,082. Both of these related applications are incorporated herein by reference.

FIELD OF THE INVENTION

The present invention relates generally to optical inspection, and specifically to methods and apparatus for inspection of solid-state surfaces, such as semiconductor wafers, and detection of features and defects thereon.

BACKGROUND OF THE INVENTION

Optical inspection is commonly used in semiconductor device manufacturing to detect defects on the surface of a wafer, such as contaminant particles, scratches and unremoved portions of Material layers. Defects can cause device failures, thus substantially reducing the process yield. Therefore, careful inspection is required to verify the cleanliness and quality both of unpatterned wafers and of patterned wafers at various stages in the manufacturing process.

A common method for inspecting semiconductor wafers is to scan a laser beam over the wafer surface, and measure the light scattered from each point on which the beam is incident. One such method, based on dark-field scattering detection, is proposed by Smilansky et al., in U.S. Pat. No. 6,366,690, whose disclosure is incorporated herein by reference. Smilansky et al. describe a wafer inspection system based on an optical detection head that comprises a laser and a number of light sensors, which are fed by fiberoptic light collectors arrayed around the laser. The optical head is positioned over the wafer surface, and the wafer is rotated and translated so that the laser beam scans over the surface. The sensors detect the radiation that is scattered from the surface in different angular directions simultaneously, as determined by the positions of the fiberoptics. The entire wafer surface is thus scanned, one pixel at a time, along a spiral path.

Another dark-field wafer inspection system is described by Marxer et al., in U.S. Pat. No. 6,271,916, whose disclosure is incorporated herein by reference. In this system, a laser beam is directed toward the wafer surface in a normal direction and scans the surface along a spiral path. An ellipsoidal mirror is used to collect the laser radiation that is scattered from the surface at angles away from the normal. Preferably, light scattered within a first range of angles is collected by one detector, while that scattered within a second range of angles is scattered by another detector. The different detector signals are used to distinguish large defects from small defects.

A further defect detection system based on this approach is described by Vaez-Iravani et al., in U.S. Pat. No. 6,538,730, which is also incorporated herein by reference. In this case, different wide- and narrow-angle collection channels are used. Signals obtained from the narrow and wide collection channels may be compared to distinguish between microscratches and particles. Forward-scattered radiation may also be collected and used for this purpose. The intensity of scattering may further be measured using sequential illumination with S- and P-polarized radiation.

Chuang et al. describe an imaging system with high numerical aperture (NA) in U.S. Pat. No. 6,392,793, whose disclosure is incorporated herein by reference. The system is based on a catadioptric group of mirrors and lenses, which can be used to collect reflected, diffracted, and scattered light over a range of angles. The system has several applications, including dark-field imaging.

Kinney et al. describe an optical inspection module and method for detecting particles and defects in U.S. Pat. No. 5,909,276, whose disclosure is incorporated herein by reference. The module includes a light source, which illuminates a surface under inspection at a grazing angle of incidence. A lens is oriented to collect non-specularly reflected light scattered from the light beam path by defects on the surface. A photodetector array in the focal plane of the lens receives the scattered light. Each pixel of the array corresponds to an area on the surface, and the plurality of pixels together form a field of view that covers substantially the entire surface.

Speckle is a well-known effect in imaging systems that use coherent illumination, due to the strong autocorrelation of the beam amplitude. In coherent illumination systems known in the art, which are typically based on continuous wave (CW) laser illumination, the laser beam is passed through a rotating diffuser, which reduces the autocorrelation and thus reduces the speckle contrast accordingly. Alternatively, the laser beam may be passed through a bundle of optical fibers of different lengths, as described, for example, by Suganuma in U.S. Pat. No. 6,249,381, whose disclosure is incorporated herein by reference. Enhanced de-speckling may be achieved by using two optical fiber bundles disposed sequentially along the light path, as described by Karpol et al., in U.S. Patent Application Publication US 2002/0067478 A1, which is assigned to the assignee of the present patent application and whose disclosure is incorporated herein by reference.

SUMMARY OF THE INVENTION

Embodiments of the present invention provide improved methods and apparatus for illumination of a surface of a sample, such as a semiconductor wafer, which enable such surfaces to be inspected with high resolution, and at high rates of data collection. In these embodiments, an inspection system comprises a source of intense optical radiation, typically based on a pulsed laser beam, which irradiates an area of a surface under inspection. One or more detector arrays are configured to receive and form respective images of the radiation scattered from the surface.

In some embodiments of the present invention, before the pulsed laser beam is incident on the surface, it is processed in order to reduce the speckles that normally arise due to the coherence of the beam. The speckle reduction subsystem used in these embodiments is adapted in a novel way to achieve very low levels of speckle contrast (as low as 1% variation in intensity over the illuminated area on the sample surface), within the tight time constraints of the laser pulse, which may be as short as 10 ns.

In some of these embodiments, the speckle contrast is reduced by passing the laser beam through a bundle of optical fibers of different lengths. In one of these embodiments, the fiber bundle comprises multimode fibers of varying lengths. In another embodiment, two fiber bundles, coupled end-to-end, may be used. The use of two fiber bundles in this manner reduces substantially the number of fibers that each bundle must comprise, by comparison with a single fiber bundle, in order to achieve a desired speckle reduction.

In another embodiment, the speckle reduction subsystem comprises a high-speed scanner, typically based on a high-speed acousto-optic transducer, which scans the angle of incidence of the pulsed laser beam over a target plane (such as the sample surface) at sufficient speed to achieve the desired speckle reduction.

In some embodiments of the present invention, the laser source is configured to emit radiation of at least two different wavelengths, so that the scattering characteristics of the surface can be evaluated at both wavelengths simultaneously. The laser beams are directed onto the surface by an optical switch, which is configurable so that the different wavelengths may be combined or directed separately, at the same angle or different angles, onto the same area of the surface. The optical switch allows the beams to be focused onto the surface at both normal and oblique incidence angles. The illumination subsystem shapes the normal and oblique beams so that both beams irradiate substantially the same area on the sample surface.

There is therefore provided, in accordance with an embodiment of the present invention, apparatus for generating optical radiation, including:

a laser, which is configured to operate in multiple transverse modes simultaneously so as to generate an input beam, which is characterized by a first speckle contrast; and optics for mixing the transverse modes of the input beam so as to generate an output beam have a second speckle contrast, which is substantially less than the first speckle contrast.

In a disclosed embodiment, the optics include a diffuser, and the optics include at least one bundle of multimode optical fibers having different, respective lengths. Typically, the laser is characterized by a beam divergence ratio $M^2$, and the second speckle contrast is less than $M^2$ times the first speckle contrast. After scrambling of the transverse modes of the laser by a diffuser, the speckle contrast of the laser beam is reduced by $M^2$. Following the fiber bundle, the speckle contrast is further reduced by the square root of the smaller of the number of longitudinal modes of the laser and the number of fibers.

There is further provided, in accordance with an embodiment of the present invention, apparatus for reducing speckle in a beam of laser radiation, including:

an optical scanner, which is coupled to scan an incidence angle of the beam on a target plane; and output optics, which are coupled to direct the beam exiting from the scanner so that the beam irradiates a single area of the target plane over a range of different angles, so as to de-correlate the radiation.

Typically, the laser radiation includes pulses shorter than 1 µs in duration, and the optical scanner is adapted to scan the beam with sufficient speed so as to reduce a contrast of the speckles formed on the area to less than 10%. Preferably, the optical scanner is adapted to scan the beam with Sufficient speed so as to reduce a contrast of the speckles formed on the area to no more than about 1%.

In some embodiments, the optical scanner includes an opto-electronic scanner, which is adapted to deflect a portion of the beam by diffraction and to scan the incidence angle of the deflected portion of the beam over the range of different angles. In one of these embodiments, the opto-electronic scanner includes an acousto-optic transducer, and a drive circuit, which is coupled to apply a frequency-chirped pulse to the transducer in order to scan the deflected portion of the beam.

There is moreover provided, in accordance with an embodiment of the present invention, apparatus for optical inspection of a sample, including:

a detector assembly, which is configured to capture an image of an area on the sample;

a laser source, which is adapted to generate first and second beams of radiation having different, respective first and second wavelengths; and an illumination module, which is coupled to direct the first and second beams of the radiation to irradiate the area on the sample, the illumination module including an optical switch, which is operative to direct both of the first and second beams simultaneously and independently so that each of the beams irradiates the area either normally or obliquely.

In one embodiment, the optical switch is configurable so as to direct the first beam to be normally incident on the surface, while directing the second beam to be obliquely incident on the surface. Typically, the illumination module includes relay optics, which are coupled to direct the radiation that is obliquely incident on the surface so that both the first and second beams irradiate the area of the surface with a substantially similar geometrical profile.

Additionally or alternatively, the illumination module includes telecentric magnifying optics with a magnification that is selectable so as to vary a size of the area irradiated by the laser source, without moving the laser source or other elements of the illumination module.

There is additionally provided, in accordance with an embodiment of the present invention, a method for generating optical radiation, including:

operating a laser in multiple transverse modes simultaneously so as to generate an input beam, which is characterized by a first speckle contrast; and mixing the transverse modes of the input beam so as to generate an output beam have a second speckle contrast, which is substantially less than the first speckle contrast.

There is further provided, in accordance with an embodiment of the present invention, a method for reducing speckle in a beam of laser radiation, including:

optically scanning an incidence angle of the beam upon a substantially stationary diffuser, so that the beam passes the diffuser over a range of different angles; and directing the beam exiting from the diffuser over the range of different angles to irradiate a single area of a target.

There is moreover provided, in accordance with an embodiment of the present invention, a method for optical inspection of a sample, including:

generating first and second beams of laser radiation having different, respective first and second wavelengths;

directing the first and second beams of the radiation to irradiate an area on the sample via an optical switch, which is operative to direct both of the first and second beams simultaneously and independently so that each of the beams irradiates the area either normally or obliquely; and capturing the radiation that is scattered from the area in order to form an image of the area.

The present invention will be more fully understood from the following detailed description of the embodiments thereof, taken together with the drawings in which:

BRIEF DESCRIPTION OF THE DRAWINGS

FIG. 3A is a schematic side view of a laser speckle reduction module, in accordance with an embodiment of the present invention;

FIG. 3B is a schematic side view of a laser speckle reduction module, in accordance with another embodiment of the present invention;

FIG. 4 is a schematic side view of optical magnification and switching elements used in an illumination module, in accordance with an embodiment of the present invention;

DETAILED DESCRIPTION OF EMBODIMENTS

Figure 1:
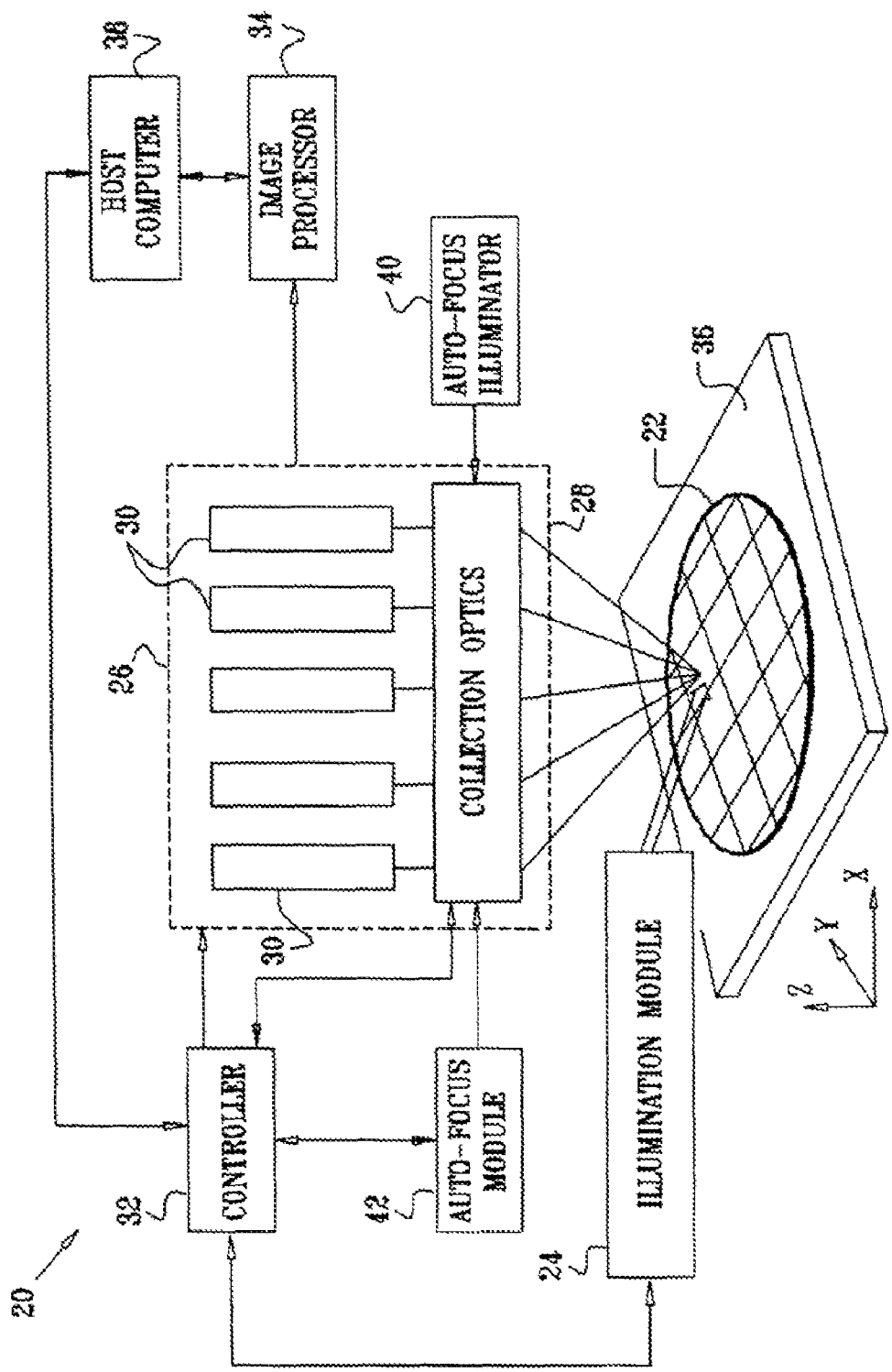
FIG. 1 is a block diagram that schematically illustrates a system for optical inspection, in accordance with an embodiment of the present invention.

FIG. 1 is a block diagram that schematically illustrates a system 20 for optical inspection of a semiconductor wafer 22, in accordance with an embodiment of the present invention. Typically, wafer 22 is patterned, using methods of semiconductor device production known in the art, and system 20 applies dark-field optical techniques to detect defects on the surface of the wafer. Alternatively, however, the principles embodied in system 20 may be applied to unpatterned wafers and to inspection of other types of samples and surfaces, as well, such as masks and reticles. Furthermore, although system 20 is dedicated to dark-field inspection, aspects of the present invention may also be applied in bright-field inspection, as well as in other areas of illumination, inspection and imaging.

System 20 comprises an illumination module 24, which illuminates the surface of sample 22 using pulsed laser radiation. Typically, module 24 is able to emit the laser radiation selectably at two or more different wavelengths, either simultaneously or one at a time. The laser radiation at any of the laser wavelengths may be directed by module 24 to impinge on wafer 22 either along a normal to the wafer surface or obliquely, as described hereinbelow. The illumination module may be configured to emit optical radiation at wavelengths in the visible, ultraviolet (UV) and/or infrared (IR) ranges. The terms "illumination" and "optical radiation" as used herein should therefore be understood as referring to any or all of the visible, UV and IR ranges.

The radiation scattered from wafer 22 is collected over a large range of angles by an optical collection module 26. Module 26 comprises collection optics 28, which image the surface of wafer 22 onto multiple cameras 30. Optics 28 may comprise either a single objective with high numerical aperture (NA) or a collection of individual objectives, one for each camera. Details of both of these alternative optical configurations, as well as of cameras 30, are described hereinbelow. Optics 28 and cameras 30 are arranged so that all the cameras image the same area on the wafer surface, i.e., the area illuminated by illumination module 24, while each camera captures the radiation that is scattered into a different angular range. Each camera 30 comprises a two-dimensional array of detector elements, such as a CCD or CMOS array, as is known in the art. Each detector element of each of the arrays is imaged onto a corresponding spot within the area irradiated by illumination module 24. Thus, the scattering characteristics of any given spot on wafer 22 as a function of angle can be determined based on the signals generated by the corresponding detector elements in the different cameras 30.

Cameras 30 are typically synchronized with the laser pulses from illumination module by a system controller 32, so that each image output frame generated by each camera corresponds to the radiation scattered from a single laser pulse. The output from each camera is received, digitized and analyzed by an image processor 34. The image processor, as described in detail hereinbelow, typically comprises dedicated hardware signal processing circuits and/or programmable digital signal processors (DSPs). A mechanical scanner, such as an X-Y-Z stage 36 translates wafer 22, typically in a raster pattern, so that each laser pulse from illumination module 24 irradiates a different area of the surface of the wafer, adjacent to (and typically slightly overlapping with) the area irradiated by the preceding pulse. Alternatively or additionally, the illumination and collection modules may be scanned relative to the wafer.

Image processor 34, processes each of the image frames that is output by each of cameras 30 in order to extract image features that may be indicative of defects on the wafer surface. The image features are passed to a host computer 38, typically a general-purpose computer workstation with suitable software, which analyzes the features in order to generate a defect list (or defect map) with respect to the wafer under inspection.

The area irradiated by module 24 and imaged by cameras 30 can be scanned using stage 36 over the entire wafer surface, or over a selected area of the surface. If the pulses emitted by module 24 are sufficiently short, substantially less than 1 for example, stage 36 may translate wafer 22 continuously in this manner without causing significant blur in the images captured by the cameras. The irradiated area typically has dimensions on the order of 2×1 mm, although the area can be enlarged or reduced using magnification optics in the illumination module, as described hereinbelow. Assuming each camera 30 to comprise an array of about 2000×1000 detector elements, the size of each pixel projected onto the wafer surface is then roughly 1×1 With module 24 operating at a repetition rate of 400 pulses/sec, the data output rate of each camera 30 to image processor 34 will be 800 Mpixels/sec. At this rate, for instance, an entire 12" semiconductor wafer can be scanned at 1 µm resolution in less than 2 min. It will be understood, however, that these typical figures of image resolution, size and speed are cited solely by way of example, and larger or smaller figures may be used depending on system speed and resolution requirements.

Controller 32 also adjusts the Z-position (height) of stage 36 in order to maintain the proper focus of cameras 30 on the wafer surface. Alternatively or additionally, the controller may adjust the camera optics for this purpose. Further alternatively or additionally, the controller may instruct image processor 34 and host computer 38 to correct for deviations in the scale and registration of the images captured by different cameras 30 so as to compensate for height variations.

In order to verify and adjust the focus, controller 32 uses an auto-focus illuminator 40 and an auto-focus sensor module 42. Illuminator 40 typically comprises a laser (not shown), such as a CW diode laser, which emits a collimated beam at an oblique angle onto or adjacent to the area of the surface of wafer 22 that is illuminated by illumination module 24, forming a spot on the wafer surface. Variations in the Z-position of wafer 22 relative to collection module 26 will then result in transverse displacement of the spot. Sensor module 42 typically comprises a detector array (also not shown), which captures an image of the spot on the wafer surface. The image of the spot is analyzed in order to detect the transverse position of the spot, which provides controller 32 with a measurement of the Z-position of the wafer surface relative to the collection module. The controller may drive stage 36 until the spot is in a pre-calibrated reference position, indicative of proper focus.

The beam emitted by illuminator 40 may pass through collection optics 28 on its way to the wafer surface, and sensor module 42 may likewise capture the image of the spot on the surface through the collection optics. In this case, illuminator 40 preferably operates in a different wavelength range from illumination module 24. Thus, appropriate filters may be used to block scatter of the auto-focus beam into cameras 30, as well as preventing interference of the pulsed beam from module 24 with the auto-focus measurement.

Alternatively, other means of auto-focus detection may be used, as are known in the art. For example, a capacitive sensor may be used to determine and adjust the vertical distance between the optics and the wafer surface.

Figure 2:
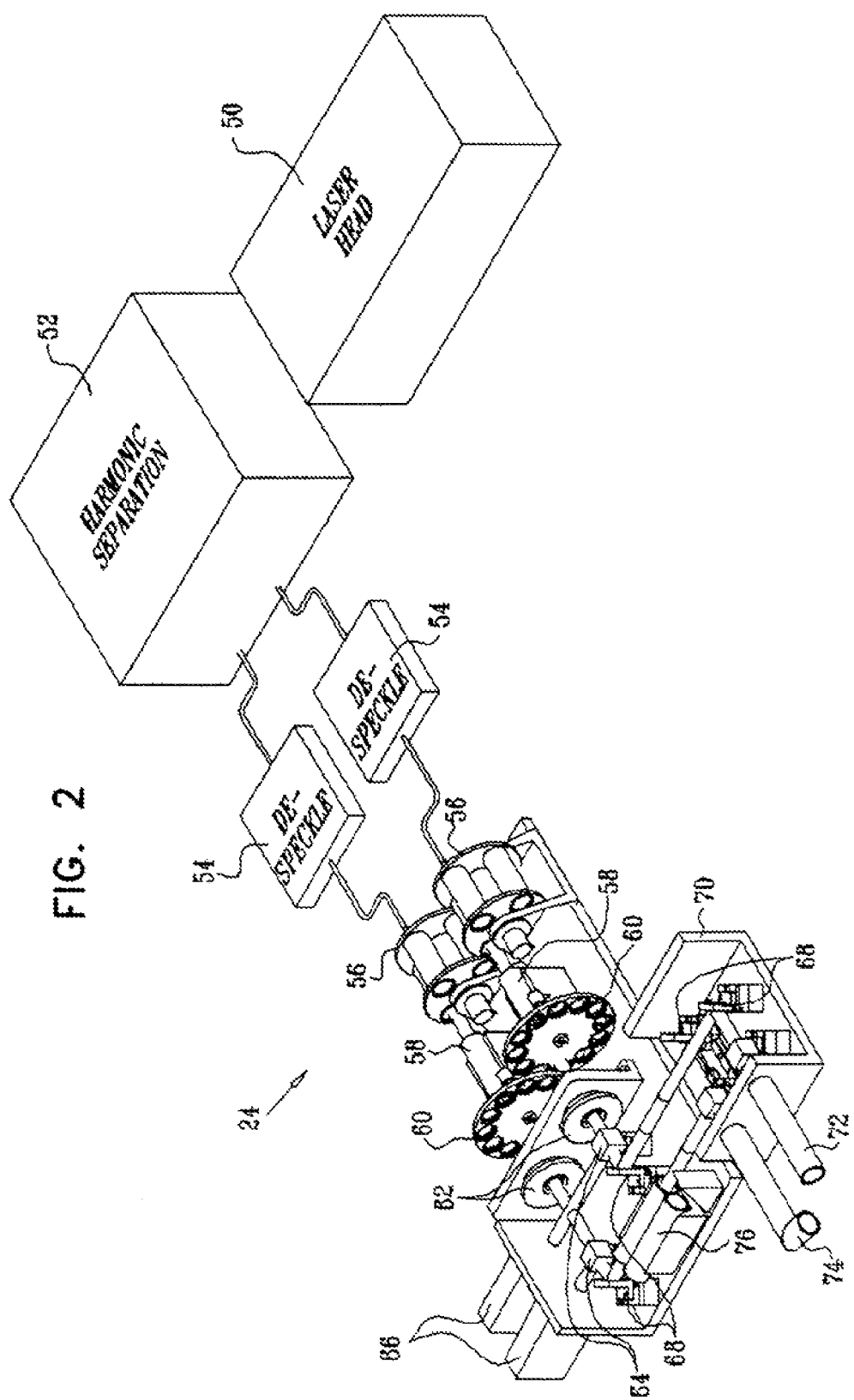
FIG. 2 is a schematic, pictorial illustration of an illumination module, in accordance with an embodiment of the present invention.

FIG. 2 is a schematic, pictorial illustration of illumination module 24, in accordance with an embodiment of the present invention. Laser head 50 comprises a pulsed laser, which is configurable to emit light at a single wavelength or at two wavelengths simultaneously. For example, the laser head may comprise a Nd:YLF laser, such as the Evolution 15 laser produced by Positive Light Inc. (Los Gatos, Calif.), with an internal frequency converter that causes the laser head to emit light at the second harmonic (527 nm) of the basic laser frequency. An external frequency converter may be added to provide a fourth harmonic output (263 nm), as well. Alternatively, module 24 may be configured to emit three or more wavelengths simultaneously, or further alternatively or additionally, to provide a wavelength-tunable output. Typically, laser head 50 is Q-switched to emit short, intense pulses, with pulse duration less than 1 µs, as noted above (and possibly as short as 10 ns). Preferably, the laser cavity is configured so that the laser operates in multiple transverse modes, to aid in reducing the coherence-related speckle on the wafer surface, as described below.

A harmonic separation module 52 separates the output of laser head 50 into two separate beams at different wavelengths. In one embodiment, module 52 simply comprises a dichroic beamsplitter, as is known in the art. The separated beams are processed by speckle reduction modules 54, as described in detail hereinbelow, to remove coherence-related speckle. Selectable telescopes 56 are used to expand the laser beams, so as to provide the desired irradiation area on the surface of wafer 22. The telescopes may be mounted on a rotatable wheel, to allow convenient selection of the desired telescope, as shown in the figure. Although the embodiment shown in FIG. 2 includes separate speckle reduction modules and telescopes for each of the different wavelengths output by laser head 50, in other embodiments the harmonic separation module may be placed farther downstream in the optical path, so that both wavelengths share a single speckle reduction module and/or a common set of telescopes.

The expanded beams output by telescopes 56 are conveyed by collimating lenses 58 to variable optical density filters 60. These filters, which may conveniently be mounted in rotatable filter wheels, allow the intensities of the two laser beams on wafer 22 to be adjusted, depending on application requirements. Polarizers 62 may similarly be rotated to determine the angles of polarization of the beams. Pick-off beamsplitters 64 deflect a small, known portion of the light in each of the laser beams toward respective energy meters 66. The energy meters provide a measurement of the intensity of each of the laser beams, for use by image processor 34 in correcting for pulse-to-pulse energy deviation, and possibly providing feedback control to laser head 50. Energy meters 66 may also be used to provide a synchronization input to cameras 30, as described below.

An optical switching module 70, comprising relay mirrors 68, allows the beam path of each of the laser wavelengths to be selected so that each wavelength may be incident on wafer 22 at either a normal or oblique angle of incidence. Switching module 70, which is described in greater detail hereinbelow, thus feeds both normal output optics 72 and oblique output optics 74. Oblique optics 74 are typically configured to illuminate the wafer surface at an angle between about 5° and 50° from the surface, although larger and smaller illumination angles are also possible. Optics 72 and 74 typically have numerical apertures (NA) in the range between about 0.01 and 0.2. The switching module may also be set to block one of the laser wavelengths, so that only a single wavelength is incident on the wafer (either normally or obliquely). When both wavelengths are used simultaneously, a chromatic compensation element 76, typically comprising suitable lenses, may be introduced into the path of one of the beams (in this embodiment the oblique beam) so that both the oblique and normal beams illuminate the same area on the wafer surface with substantially the same geometrical profile.

FIG. 3A is a schematic side view of speckle reduction module 54, in accordance with an embodiment of the present invention. The module shown in this figure can be applied to a single one of the laser wavelengths, in the configuration shown in FIG. 2, or it can alternatively be applied to both wavelengths together, as long as the optical elements in the module are properly designed for both wavelengths.

As noted above, in coherent illumination systems known in the art, based on continuous wave (CW) laser illumination, the laser beam is passed through a rotating diffuser, which reduces the autocorrelation and thus reduces the speckle contrast accordingly. In system 20, however, the short duration of the pulses emitted by laser head 50 makes this conventional solution ineffective, since an impractically high speed of rotation of the diffuser would be required in order to reduce the speckle contrast sufficiently.

Therefore, in the embodiment of module 54 shown in FIG. 3A, an acousto-optic transducer 82 is driven to scan the incidence angle of the laser beam on a target plane 84 at high speed. The high-speed scan causes the beam to be incident on the target plane (and hence on wafer 22) over a sufficient range of angles during the duration of the laser pulse in order to achieve the desired speckle contrast reduction. The beam that is input to module 54 from laser head 50 is typically expanded by a cylindrical beam expander 86. Transducer 82 is driven to diffract a portion of the laser beam by a driver 88, which is synchronized with the laser pulses. Driver 88 generates electrical driving signals that are frequency-chirped, so that transducer 82 diffracts a first order 90 of the laser beam at an angle that varies over the duration of the laser pulse. An imaging lens 97 images diffracted first order 90 onto target plane 84. A diaphragm 94 at the Fourier plane of lens 97 stops an undeflected zero order 96 of the beam from passing. Alternatively, for enhanced efficiency (in terms of output intensity from module 54 relative to the input), a second acousto-optic transducer may be added in order to scan the zero-order beam, as well.

As a result of the frequency chirp applied by driver 88, the angle of incidence of the diffracted first-order beam on target plane 84 varies rapidly during the laser pulse. For a given chirp bandwidth $\Delta f$ and scan time T (equal to the laser pulse duration), the number of resolution points (NRP) of the acousto-optic scan is given approximately by NRP=$\Delta f$T. The laser beam, in other words, is broken up into NRP different angular components, which are mutually non-correlated. Output optics 98 collect and focus the angular beam components from target plane 84 into telescope 56. The reduction in the speckle contrast on target plane 84 (and hence on wafer 22) is given approximately by $\sqrt{NRP}$. For example, given a laser pulse duration of 100-300 ns, a chirp bandwidth $\Delta f$ between 400 and 800 MHz will reduce the beam speckle to the range of 6-16% of the input beam contrast. The polarization of the input laser beam is preserved in the output.

As a further option, transducer may be replaced by other types of high-speed scanners, as are known in the art, such as rotating mirror scanner. The degree of speckle reduction, however, depends on the speed of the scan.

FIG. 3B is a schematic side view of speckle reduction module 54, in accordance with another embodiment of the present invention. This embodiment uses fiberoptic bundles 100 and 102 to convey the beam from laser 50 to telescope 56. Alternatively, a single fiberoptic bundle may be used, as described further hereinbelow. Typically, bundles 100 and 102 comprise quartz or other UV-lucent fibers.

The individual fibers in each bundle 100 and 102 are of different lengths, thus creating N different speckle patterns, which are mixed by a diffuser 104. Consequently, the speckle contrast in the beam that is output to telescope 56 is reduced by a factor of $N^{1/2}$. If a single bundle of single-mode optical fibers were used in module 54, as it is in systems known in the art, 10,000 fibers of different lengths would be required in order to reduce the output speckle contrast to 1% of the input contrast. This solution is costly and difficult to implement. For this reason, two bundles 100 and 102 are used here end-to-end, creating N=n×m different speckle patterns, wherein n and m are the number of individual fibers in bundles 100 and 102, respectively. Thus, if each of bundles 100 and 102 contains one hundred fibers, the desired reduction to 1% output contrast can be achieved. Better speckle reduction may be gained, however, with fewer practical difficulties, by using a bundle of multi-mode fibers, as described below.

An input coupler 108 focuses the beam from laser 50 through diffuser 104 into fiber bundle 100. Any suitable type of diffusing element may be used for this purpose, such as a microlens array or mode scrambler, as are known in the art. Assuming the coherence length of the laser beam to be 1 mm, bundle 100 may, for example, contain one hundred fibers, which are evenly graduated in length in steps of 1-2 mm. A Fourier lens 110 focuses the output of bundle 100 into bundle 102, such that the output of each fiber in bundle 100 is distributed among substantially all the fibers in bundle 102. The fibers in bundle 102 are also graduated in length. An output coupler 112 collects the radiation output from bundle 102 into telescope 56. Although couplers 108 and 112 and Fourier lens 110 are shown in the figure as simple lenses, in practice the couplers and Fourier lens may comprise multi-element, telecentric optics. Further details of a de-speckling system based on end-to-end fiber bundles are provided in the above-mentioned U.S. Patent Application Publication US 2002/0067478 A1.

In an alternative embodiment, not shown in the figures, module 54 may comprise a single bundle of multi-mode fibers. This embodiment is similar in structure to that shown in FIG. 3B, except that Fourier lens 110 and bundle 102 are removed. It is useful particularly when laser 50 generates multiple transverse modes. Each of the multi-mode fibers in bundle 100 supports multiple propagation modes, having different optical path lengths through the fiber. The inventors have found that a bundle of between one and two hundred multimode fibers (depending on fiber properties such as fiber diameter, NA and lengths), operating together with such a multi-mode laser, is able to generate the N=10,000 different speckle patterns required to reduce the output contrast to 1%. The use of multi-mode fibers, however, destroys the input beam polarization.

The number of transverse modes in which a multi-mode laser emits radiation is given approximately by a factor $M_x^2 \cdot M_y^2$, wherein $M^2$ is the well-known ratio of the angular divergence of the multi-mode laser beam relative to a single-mode laser with the same beam waist diameter in each of the x- and y-directions. Thus, for example, a laser having $M_x^2=M_y^2=30$ will produce nearly 1000 different transverse modes. Each transverse mode is self-coherent (to within the coherence length of the laser), but is spatially non-overlapping and non-coherent with the other transverse modes. Mixing the transverse modes by passing the beam through a diffuser, even in the absence of a fiber bundle, will reduce the beam speckle contrast by $\sqrt{M_x^2 M_y^2}$ i.e., by about a factor of 30. Alternatively, the laser beam may be focused through the diffuser by a Fourier lens into a bundle of multi-mode fibers of different lengths, as described above. In this case, speckle reduction module 54 mixes both the transverse and the longitudinal modes of the laser, giving a reduction of $\sqrt{NM_x^2 M_y^2}$ in the speckle contrast, wherein N is the number of fibers in the bundle. For N=100 and $M_x^2=M_y^2=10$, the speckle contrast of the laser beam is reduced to 1% of its input value.

Alternatively or additionally, speckle reduction modules 54 may implement other methods of speckle reduction, as are known in the art. Note that modules 54 may also serve the purpose of homogenizing the laser beams, giving a substantially uniform intensity profile over the area of the beams and hence of the area irradiated on the surface of wafer 22.

FIG. 4 is a schematic side view showing further elements of illumination module 24, in accordance with an embodiment of the present invention. Certain aspects of this embodiment differ from the embodiment shown in FIG. 2, while other elements shown in FIG. 2 are omitted here for the sake of simplicity. Those skilled in the art will understand that various other combinations of the features and elements shown in FIGS. 2 and 4 may also be used in system 20.

In the embodiment shown in FIG. 4, a single telescope assembly 120, comprising telescopes 56 of different magnifications, is used for both output wavelengths of laser head 50. Alternatively, as shown above in FIG. 2, separate telescopes 56 may be used for each of the output wavelengths. Typically, telescopes 56 comprise telecentric, Köhler-type optics, so that every point in an object plane 124 (at the output from speckle reduction module 54) illuminates all points in a Fourier plane 126, at the output of the telescopes. All of telescopes 56 have the same focal planes, so that object plane 124 and Fourier plane 126 do not move when the magnification of assembly 120 is changed. The telescopes are also color-corrected, so that they have the same focal planes at both of the laser wavelengths. The telescopes may be mounted on a rotating wheel 122, to allow the magnification to be changed easily when desired, under the control of controller 32.

A dichroic beamsplitter 128 in this embodiment takes the place of harmonic separation module 52 shown in FIG. 2. Beamsplitter 128 passes one of the laser wavelengths to a first optical path 130, and the other wavelength to a second optical path 132. Each optical path includes a filter 60 and polarizer 62, as described above. An optical switch 134 determines which wavelength is to be conveyed to normal optics 72, and which to oblique optics 74. Switch 134 comprises a turning mirror 136, which may be positioned in either of two settings, labeled 136a and 136b. When the turning mirror is in setting 136a, it deflects the radiation in optical path 132 into oblique optics 74, while allowing the radiation in path 130 to pass through to be directed into normal optics 72. Switching the turning mirror in switch 134 to setting 136b causes the radiation in path 132 to pass through to normal optics 72, while the radiation path 130 is deflected into oblique optics 74. Switch 134 may have further settings that convey the radiation in both of paths 130 and 132 together to either normal optics 72 or oblique optics 74. A dichroic beam combiner 138 directs one or both of the paths into the normal channel, as required. Switch 134 may also comprise a beam block (not shown), for blocking either of paths 130 or 132 when it is desired to irradiate wafer 22 with only a single wavelength.

Normal and oblique optics 72 and 74 comprise relay lenses 140 for conveying the laser beams onto the desired area of wafer 22. In addition, oblique optics 74 comprise a turning mirror 142, which directs the laser beam onto the surface at the appropriate oblique angle. Typically, optics 72 and 74 are non-imaging optics, and are aligned so that both the normal and oblique beams irradiate substantially the same area on the wafer surface. (For example, oblique optics 74 may be aligned so that the laser beam passes through them off axis, to compensate for the oblique angle of incidence.) The area of the wafer that is imaged by cameras 30 may vary and in some cases may be rectangular, rather than square, as described below. Therefore, relay lenses 140 may comprise anamorphic elements, such as one or more cylindrical lenses, in order to match the area illuminated by the laser beams to the area imaged by cameras 30.

Figure 5:
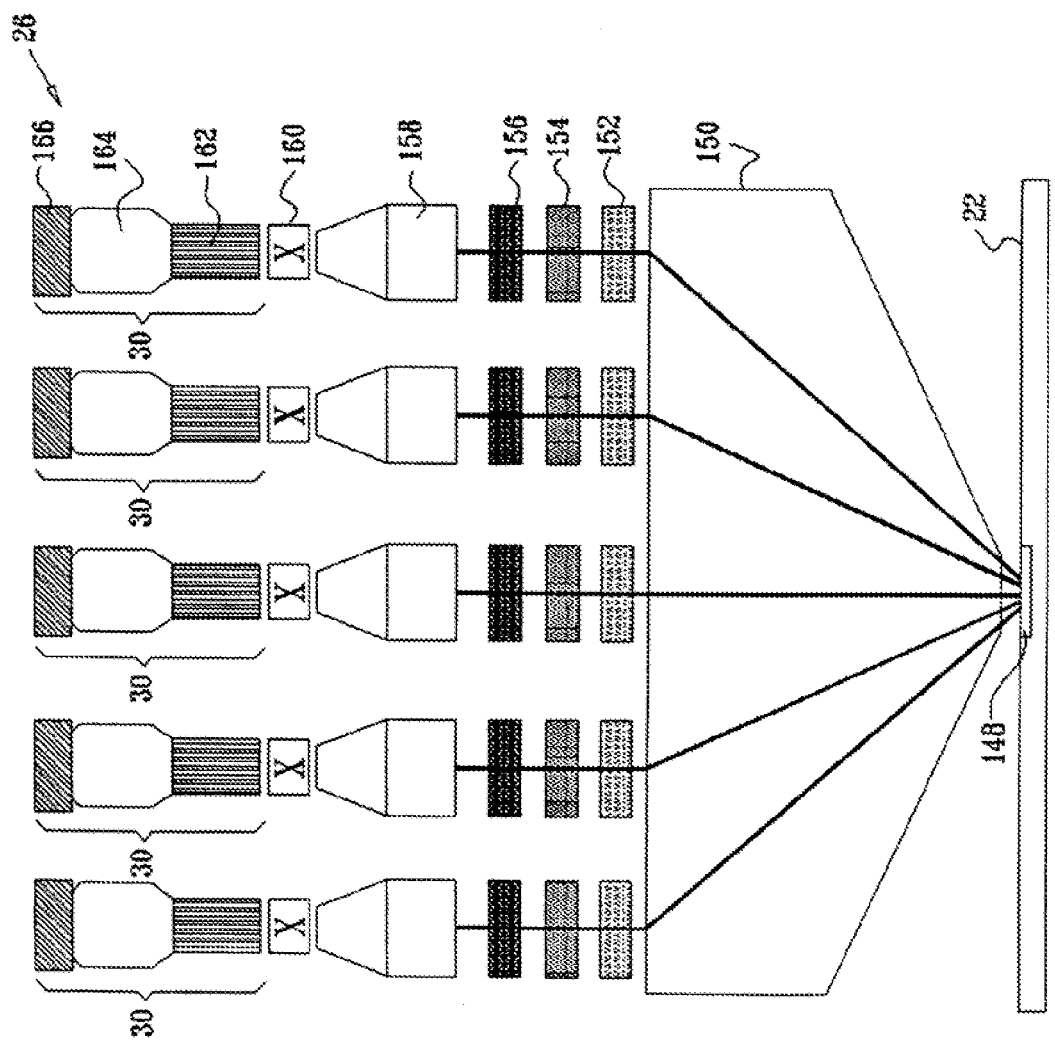
FIG. 5 is a schematic side view of an optical collection module, in accordance with an embodiment of the present invention.

FIG. 5 is a schematic side view of collection module 26, in accordance with an embodiment of the present invention. In this embodiment and in the embodiment shown in FIG. 1, module 26 is shown as comprising five cameras 30. Alternatively, module 26 may comprise a smaller or greater number of cameras, typically as many as ten cameras. As noted above, all the cameras image scattered radiation from a common area 148 on the surface of wafer 22, but each camera is configured to collect the radiation along a different angular axis (i.e., a different elevation and/or azimuth). Although system 20 is designed mainly for use in dark-field detection, one or more of cameras 30 may be used for bright-field detection, as well, in conjunction with either the normal-incidence or oblique-incidence illumination beam.

An objective 150 collects and collimates the scattered light from area 148. In order to collect scattered light at low elevation, objective 150 preferably has a high NA, most preferably as high as 0.95. An exemplary design of objective 150, using multiple refractive elements, is described hereinbelow with reference to FIG. 6. Alternatively, objective 150 may comprise a reflective or catadioptric element, as described, for example, in the above-mentioned U.S. Pat. No. 6,392,793. Each of cameras 30 is positioned, as shown in FIG. 5, to receive a particular angular portion of the light collected by objective 150.

For each camera 30, a bandpass filter 152 selects the wavelength range that the camera is to receive. Typically, filter 152 selects one of the two wavelengths emitted by illumination module 24, while rejecting the other wavelength. Filter 152 may also be implemented as a dichroic beamsplitter, and configured so that one of cameras 30 receives the scattered light along a given angle at one wavelength, while another camera receives the scattered light along the same angle at the other wavelength. As a further alternative, filter 152 may be chosen to pass radiation in another wavelength range, such as a band in which wafer 22 is expected to fluoresce. For example, when organic materials, such as photoresist, are irradiated at 266 nm, they tend to fluoresce in the range of 400 nm. Thus, setting filter 152 to pass light in the 400 nm band allows camera 30 to detect defects in the organic material or residues thereof.

A spatial filter 154 can be used to limit the collection angle of each camera 30, by blocking certain regions of the collimated scattered light. The spatial filter is especially useful in eliminating background diffraction from repetitive features on patterned wafers. The spatial filter is chosen, based on the known diffraction pattern of the features on the wafer surface, to block these strong diffraction nodes, in order to enhance the sensitivity of system 20 to actual defects, as is known in the art. This use of spatial filtering for this purpose is described, for example, in U.S. patent application Ser. No. 10/050,890, filed Jan. 15, 2002, which is assigned to the assignee of the present patent application and whose disclosure is incorporated herein by reference. This patent application describes a method for creating spatial filters adaptively, in response to the diffraction lobes of different sorts of wafer patterns. This method may be implemented in filters 154 in module 26. Alternatively, spatial filters 154 may comprise fixed patterns, as is known in the art.

A rotatable polarizer 156 is provided in the optical path in order to select the direction of polarization of scattered light that is to be received by camera 30. The polarizer is useful, for example, in improving detection sensitivity by rejecting background scatter due to rough and/or highly-reflective surface structures on wafer 22. Optionally, polarizer 156 is implemented as a polarizing beamsplitter, which is configured so that two cameras 30 receive the light scattered along a given angle in orthogonal polarizations.

As a further option (not shown in the figures), the optical path may comprise a beamsplitter, which divides the light scattered along a given collection angle between two or more different cameras 30. The beamsplitter may be used for wavelength division, as mentioned above, or to divide the same wavelength between the two or more cameras in a predetermined proportionality. Different spatial filters 154 may be used following the beamsplitter in the beam paths to the different cameras, in order to filter out diffraction lobes due to different sorts of patterns on the wafer. As a further alternative, the beamsplitter may divide the light scattered along a given angle unequally between two or more of the cameras, for example, in a ratio of 100:1. This arrangement effectively increases the dynamic range of system 20, since the camera receiving the smaller share of the radiation is still able to generate meaningful image data even in areas of bright scatter, in which the camera receiving the larger share of the radiation is saturated. An arrangement of this sort is described, for example, in U.S. patent application Ser. No. 10/050,889, filed Jan. 15, 2002, which is assigned to the assignee of the present patent application and whose disclosure is incorporated herein by reference.

A focusing lens 158 focuses the collected and filtered light onto camera 30. Lens 158 may be adjustable, either manually or under motorized control. A variable magnifier 160 may be used to change the size of the magnified image received by the camera. Alternatively, the functions of lens 158 and magnifier 160 may be combined within a single optical unit for each camera. The magnifier determines the resolution of the image captured by camera 30, i.e., the size of the area on the wafer surface that corresponds to each pixel in the output image from the camera. Magnifier 160 is typically operated in conjunction with telescopes 56 in illumination module 24, so that size of the illuminated area is roughly equal to the area imaged by the cameras.

Each camera 30 comprises an image intensifier 162, whose photocathode is aligned at the image plane of the focusing lens and magnifier. Any suitable type of image intensifier tube may be used for this purpose, including both first- and second-generation types, such as the C6654 image intensifier produced by Hamamatsu Photonics K.K. (Shizuoka-ken, Japan). To provide optimal imaging in the demanding environment of system 20, intensifier 162 preferably has high bandwidth and high resolution, and is preferably capable of gated operation, with high current and low phosphor memory, at the repetition rate of laser head 50—typically up to about 1000 pulses per sec. The useful diameter of intensifier 162 is preferably at least 18 mm, but a larger diameter, in the range of 25-40 mm, may be even more advantageous.

The output of image intensifier 162 is focused by relay optics 164 onto an image sensor 166. The relay optics may comprise, for example, either a relay lens or a fiberoptic faceplate coupled directly to the image sensor chip. Image sensor 166 comprises a two-dimensional matrix of detector elements, such as a CCD or CMOS array, as is known in the art. For example, the image sensor may comprise a CMOS digital image sensor, such as model MI-MV13, made by Micron Technology Inc. (Boise, Id.). This sensor has 1280× 1024 pixels, with 12 μm vertical and horizontal pitch, and a frame rate up to 500 frames per second for full frames.

The use of image intensifiers 162 in cameras 30 increases the sensitivity of the cameras substantially over cameras using image sensors 166 alone without intensification. The intensifiers may be gated, in synchronization with the light pulses from illumination module 24, in order to increase the sensitivity of the cameras and reduce their noise levels still further. Typically, the photocathodes of intensifiers 162 are chosen to have high quantum efficiency at the wavelengths emitted by the illumination module, while the phosphors of the intensifiers may be chosen to emit light in a different wavelength range in which image sensors 166 have high responsivity. Thus, the image intensifiers, in addition to amplifying the incident scattered light, are also useful in downconverting the ultraviolet (UV) and blue light that is scattered from wafer 22 to the green or red range, to which the silicon image sensors are more responsive. In addition, intensifiers 162 act as low-pass spatial filters, and may thus help to smooth high-frequency structures in the scattered light that might otherwise cause aliasing in the images output by sensors 166.

Intensifiers 162 preferably have high resolution, as dictated by the resolution of sensors 166. For example, to take full advantage of the resolution of the above-mentioned MV13 sensor, intensifier 162 should be designed to provide 1640 distinct pixels along the image diagonal. This resolution criterion may also be expressed in terms of the modulation transfer function (MTF) of the intensifier, giving MTF=30% for a test image with 33 line pairs/mm. Bright points in the image captured by cameras 30 can result in formation of a bright halo, generally due to reflections inside the image intensifier tube, which may compromise the resolution of the image. Intensifiers 162 are preferably designed to suppress such reflections so that the halo diameter is no more than 0.2 mm in any case. Furthermore, in order to exploit the full range of sensitivity of sensor 166, intensifier 162 should exhibit linear behavior up to high maximum output brightness (MOB), typically on the order of 600 $\mu W/cm^2$.

Figure 6:
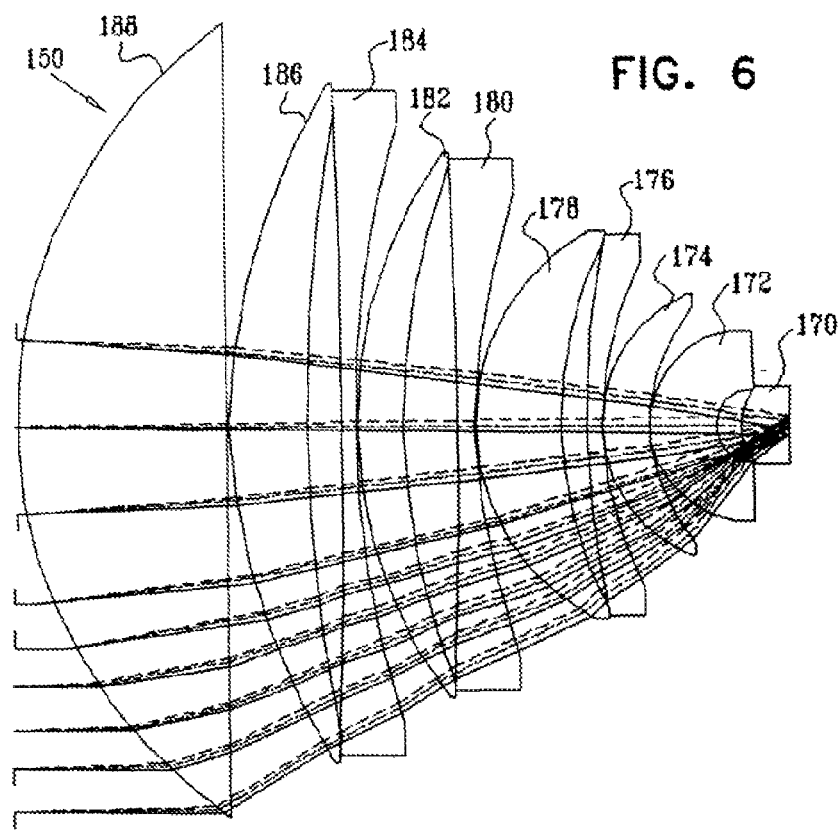
FIG. 6 is a schematic optical diagram of a high-NA objective, in accordance with an embodiment of the present invention.

FIG. 6 is a schematic optical diagram showing details of objective 150, in accordance with an embodiment of the present invention. In this embodiment, objective 150 comprises ten elements, all made from fused silica (refractive index 1.499679), having dimensions (in mm) as listed below. The first surface of each element is the surface closer to the object plane (at the right side of the figure), and radii of curvature are listed as positive for surfaces whose center of curvature is located to the right of the surface.

Lens 170
    First surface curvature: −554.32; distance from object plane: 0.10.
    Thickness: 28.92.
    Second surface curvature: 38.23.

Lens 172
    First surface curvature: 22.17; distance from second surface of lens 172: 14.35.
    Thickness: 42.86.
    Second surface curvature: 59.97.

Lens 174
    First surface curvature: 116.11; distance from second surface of lens 172: 0.10.
    Thickness: 28.99.
    Second surface curvature: 90.24.

Lens 176
    First surface curvature: 233.96; distance from second surface of lens 174: 0.10.
    Thickness: 10.00.
    Second surface curvature: 578.50.

Lens 178
    First surface curvature: 260.16; distance from second surface of lens 176: 15.94.
    Thickness: 53.07.
    Second surface curvature: 136.10.

Lens 180
    First surface curvature: 446.16; distance from second surface of lens 178: 0.10.
    Thickness: 10.00.
    Second surface curvature: −2850.63.

Lens 182
    First surface curvature: 473.81; distance from second surface of lens 180: 34.11.

Thickness: 28.54.
Second surface curvature: 294.90.
Lens 184
First surface curvature: 701.43; distance from second surface of lens 182: 0.10.
Thickness: 10.00.
Second surface curvature: −4117.15.
Lens 186
First surface curvature: 1275.43; distance from second surface of lens 184: 21.78.
Thickness: 48.42.
Second surface curvature: 395.84.
Lens 188
First surface curvature: −11047.73; distance from second surface of lens 186: 0.10.
Thickness: 132.30.
Second surface curvature: 313.99.
Objective 150, as shown in FIG. 6, has NA=0.95.

Figure 7:
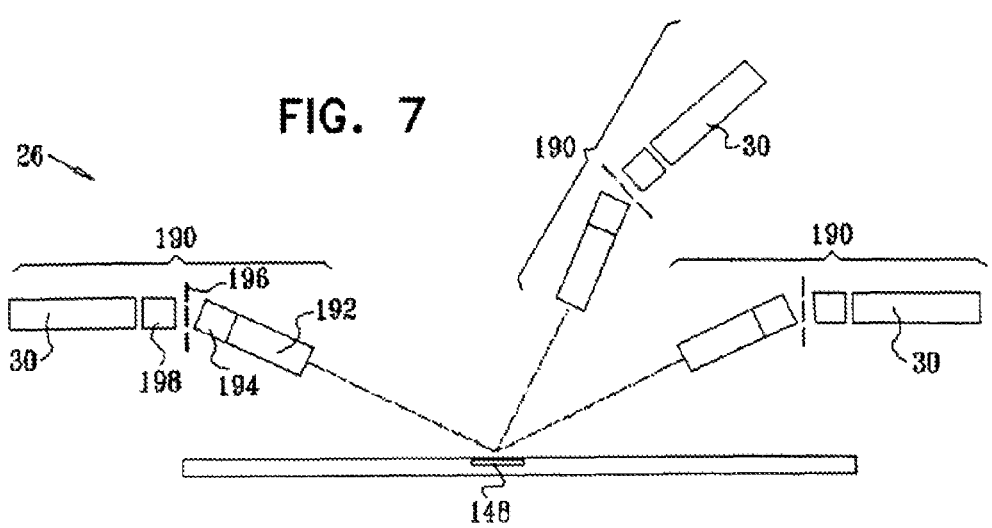
FIG. 7 is a schematic side view of an optical collection module, in accordance with another embodiment of the present invention.

FIG. 7 is a schematic side view of collection module 26, in accordance with another embodiment of the present invention. In this case, module 26 comprises multiple, separate imaging channels 190, each with its own collection optics, rather than a single shared objective as in FIGS. 5 and 6. Channels 190 are distributed to collect the light scattered from wafer 22 at different, respective angles. As its objective, each channel comprises an afocal relay 192 and a tilt correction unit (TCU) 194, which form an intermediate image 196 of the wafer surface. A magnification module (MGM) 198 focuses the intermediate image, with adjustable magnification, onto the entrance plane of camera 30. As noted above, the entrance plane of the cameras in system 20 is typically the photocathode plane of an image intensifier that forms part of the camera, as described above.

Afocal relay 192 and TCU 194 are designed to solve two problems that arise when imaging a surface at an oblique angle:
1. The object distance from points on the surface to the entrance pupil of the objective varies over the field of view of the objective.
2. The intermediate image formed by the objective is tilted and skewed, due to the tilt of the surface relative to the optical axis of the objective.

The afocal relay and TCU solve these problems, as described in greater detail hereinbelow, so that intermediate image 196 in all of channels 190 is a flat, undistorted image of the same area 148 on the wafer surface, with uniform magnification, notwithstanding the different angles at which channels 190 capture their images. The same optical design may be used for all of afocal relays 192, irrespective of viewing angle, and for all of magnification modules 198. The design of TCU 194 varies as a function of elevation of the viewing angle of the respective channel 190, due to the variation with elevation of the tilt of the object plane relative to the optical axis of the channel.

Figure 8:
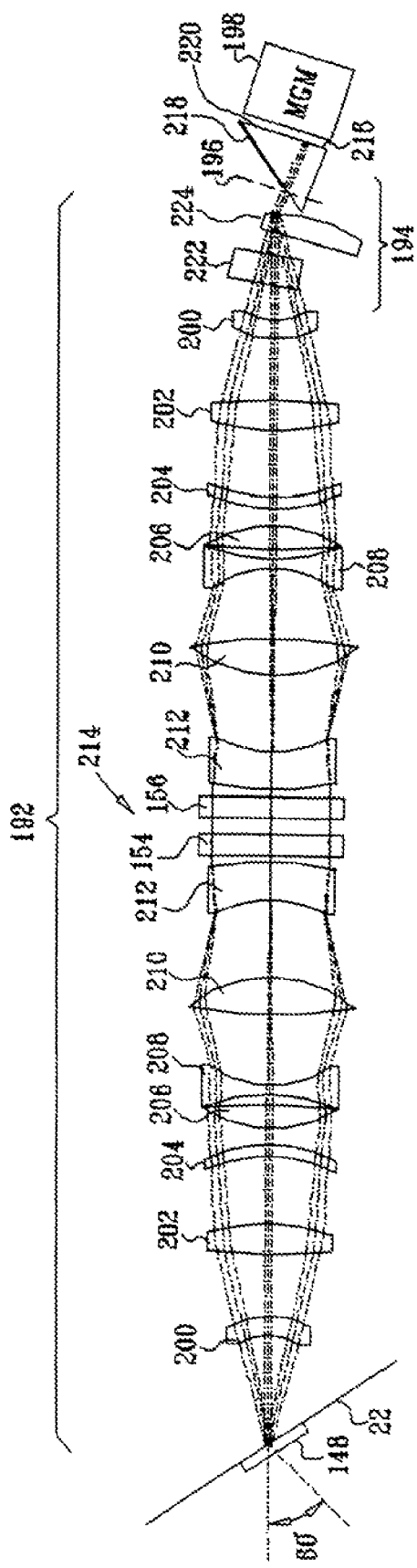
FIG. 8 is a schematic optical diagram of an afocal relay lens and tilt correction unit, in accordance with an embodiment of the present invention.

FIG. 8 is a schematic optical diagram showing details of afocal relay 192 and TCU 196, in accordance with an embodiment of the present invention. The afocal relay is of telecentric design, with unit magnification, so that it creates no keystone distortion and magnifies the image of area 148 uniformly, despite the tilt of the object plane. Afocal relay is optically symmetrical about its pupil 214, and comprises the following elements (starting from the left side in the figure), having dimensions (in mm) as listed below. The first surface of each element is the surface closer to the object plane (at the left side of the figure), and radii of curvature are listed as positive for surfaces whose center of curvature is located to the right of the surface.

Lens 200
First surface curvature: −29.53; distance from object plane: 60.48.
Thickness: 9.99.
Second surface curvature: −36.37.
Lens 202
First surface curvature: 469.41; distance from second surface of lens 200: 32.98.
Thickness: 14.85.
Second surface curvature: −100.00.
Lens 204
First surface curvature: −69.56; distance from second surface of lens 202: 36.50.
Thickness: 4.41.
Second surface curvature: −76.35.
Lens 206
First surface curvature: 61.15; distance from second surface of lens 204: 10.20.
Thickness: 11.78.
Second surface curvature: −345.29.
Lens 208
First surface curvature: −89.75; distance from second surface of lens 206: 4.72.
Thickness: 5.50.
Second surface curvature: 54.75.
Lens 210
First surface curvature: 255.13; distance from second surface of lens 208: 38.23.
Thickness: 18.21.
Second surface curvature: −63.34.
Lens 212
First surface curvature: −60.74; distance from second surface of lens 210: 41.26.
Thickness: 19.39.
Second surface curvature: −165.26.

The distance from the second surface of lens 212 to pupil 214 is 20.00 mm. The elements to the right of the pupil are identical, in mirror image, to the elements described above.

Afocal relay 192, as shown in FIG. 8, has NA between about 0.25 and 0.3, depending on wavelength. Spatial filter 154 and polarizer 156 (as well as a wavelength filter, if desired) may be inserted, as shown, in the Fourier plane of relay 192, which is located at pupil 214.

TCU 194 comprises a prism 216, whose entrance face 218 is oriented approximately parallel to the image plane of afocal relay 192. (As noted above, the angle of this image plane relative to the optical axis of relay 192 is equal to the angle of the object plane—i.e., the angle of the surface of wafer 22—relative to the optical axis. In the present example, the object and image planes are tilted by 60° relative to the optical axis.) Refraction of the rays that are output by relay 192 creates intermediate image 196 as an imaginary image, which may be roughly parallel to an exit face 220 of prism 216. In the present embodiment, with 60° between the optical axis of relay 192 and the normal to wafer 22, the vertex angle between faces 218 and 220 of prism 216 is 46.56°. It can be seen that the prism angle and orientation will vary as a function of the elevation angle of the optical axis of relay 192 relative to the wafer surface.

To compensate for pseudo coma introduced by prism 216, TCU 194 comprises a pair of fused silica cylindrical lenses 222 and 224, having the following characteristics (with dimensions in mm):
Lens 222 (plano-concave)
First surface curvature: flat; distance from second surface of lens 200 (final lens in relay 192): 18.51.

Thickness: 13.78.
Second surface curvature: 92.90.
Decenter: 5.65; tilt: −4.93° (relative to axis of relay 192).
Lens 224 (plano-convex)
First surface curvature: flat; distance from second surface of lens 200: 39.27.
Thickness: 11.38.
Second surface curvature: −103.17.
Decenter: −15.39; tilt: −16.77°.

In this configuration, face 218 of prism 216 is located 71.27 mm from the second surface of lens 200, with a decenter of −3.84 mm and tilt of −69.69°.

Figure 9:
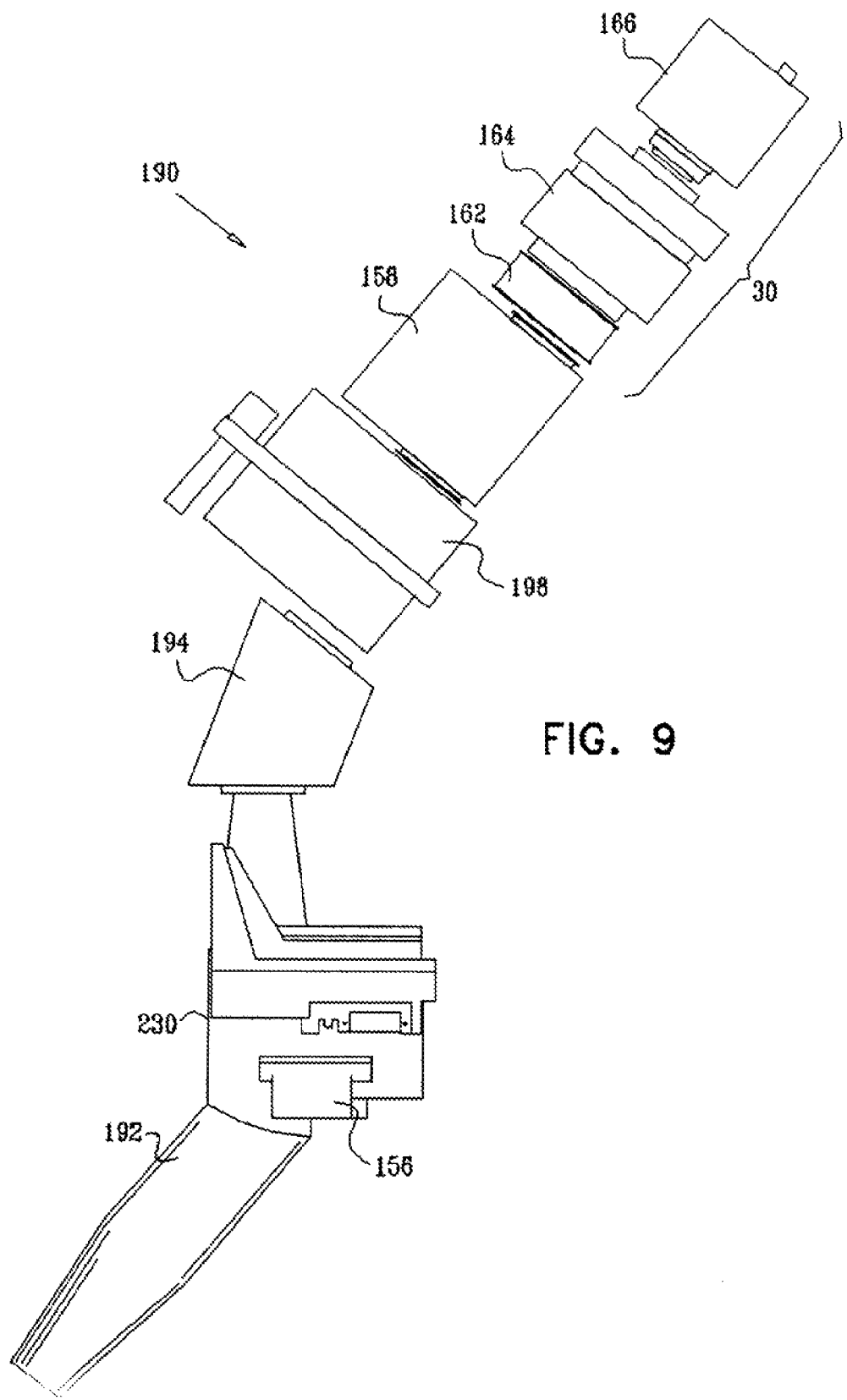
FIG. 9 is a schematic, pictorial illustration of an optical collection channel used in an optical inspection system, in accordance with an embodiment of the present invention.

FIG. 9 is a schematic side view of one of imaging channels 190, showing aspects of the mechanical design of the optics and camera 30, in accordance with an embodiment of the present invention. In this embodiment, for reasons of mechanical convenience, afocal relay 192 includes a turning mirror (not shown), which bends the optical axis of the relay into the bent form illustrated in the figure. Functionally, however, relay 192 operates in substantially the manner described above. A filter unit 230, positioned at the center of relay 192, accommodates polarizer 156, as well as wavelength filter 152 (not shown in this figure) and spatial filter 154 as required.

The positions of focusing lens 158 and magnification module 198 are reversed in this embodiment, relative to the positions of the focusing lens and magnifier 160 in FIG. 5, but their functions are substantially the same. Module 198 comprises multiple different lenses, with different magnifications, which may be selected by rotating the module, as in telescope assembly 120 (FIG. 4). Assuming the resolution of intensifier 162 to be about 15 while camera 30 is intended to form images of the wafer surface with resolution (measured in the object plane) between 0.5 μm and 4 μm, it is desirable that module 198 provide magnifications between approximately 4× and 32×. Magnification module 198 may comprise a selection of custom objectives and/or off-shelf microscope objectives, which are chosen to meet these magnification requirements, for example.

Figure 10:
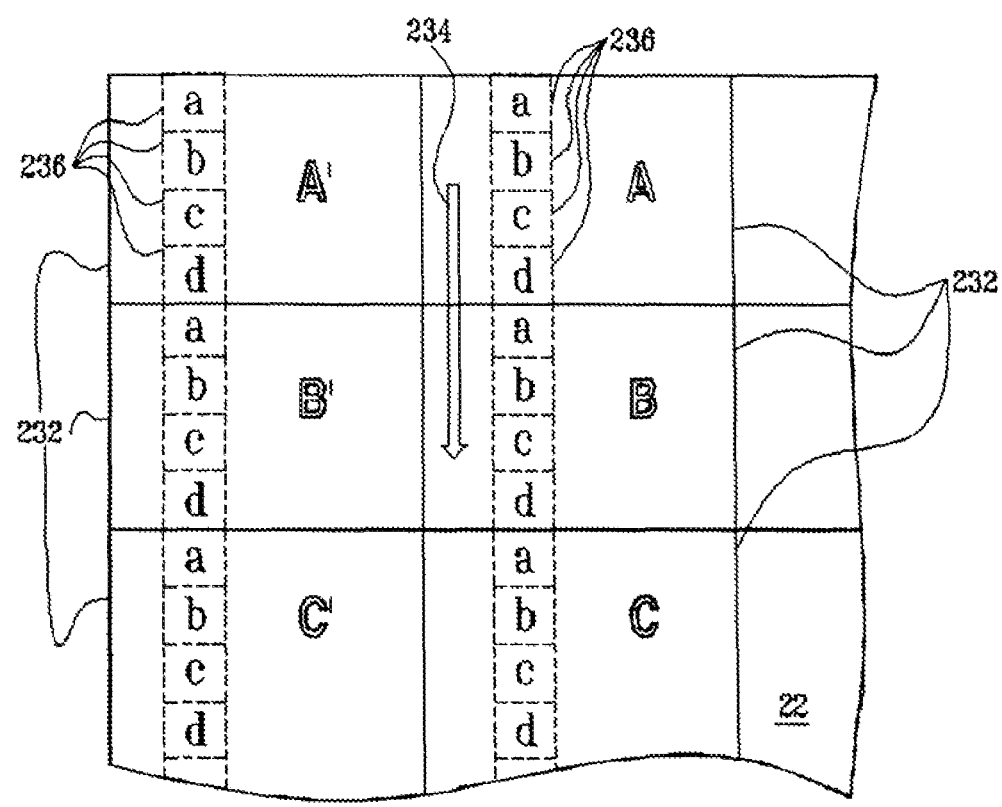
FIG. 10 is a schematic top view of a semiconductor wafer under inspection, showing areas of images captured of the wafer surface, in accordance with an embodiment of the present invention.

FIG. 10 is a schematic top view of wafer 22, showing a pattern of images 236 scanned by system 20, in accordance with an embodiment of the present invention. Wafer 22 is divided into dice 232, as is known in the art. Stage 36 (FIG. 1) scans wafer 22 in a raster pattern, with a scan direction indicated by an arrow 234 in FIG. 10. Alternatively, successive scan lines may be traversed in opposing directions. In the present example, cameras 30 first capture images 236 of dice A', B' C', . . . , on one scan line of the raster, and then capture images A, B, C, . . . , on a subsequent scan line. In each scan line, four adjacent, successive images 236, labeled a, b, c and d, cover the width of each die. Typically, the raster pattern is chosen so that the successive scan lines cover substantially the entire surface of wafer 22. FIG. 10 shows only two scan lines, however, for the sake of clarity of illustration.

Illumination module 24 and cameras 30 (FIG. 1) are synchronized with stage 36 so that images 236 are aligned with dice 232 on wafer 24. In other words, as shown in FIG. 10, images 236 are aligned with the die boundaries in such a way that each image a, b, c and d covers a predetermined area of the die. The area of each image is consistent with the area covered by the same image in the earlier corresponding scan line. Therefore, image a captured of die B by any one of cameras 30 is expected to include substantially the same features, in the same locations in the image, as does image a on die A that was captured by the same camera. This correspondence facilitates die-to-die comparison, as described below. As noted above, all of cameras 30 simultaneously capture respective images of the same areas on wafer 22. The pattern shown in FIG. 10 is thus characteristic of the images captured by any and all of the cameras, although there may be some distortion from camera to camera because of the different viewing angles. The distortion is typically corrected only after die-to-die comparison, as described below.

Alignment of images 236 with the boundaries of dice 232 is accomplished by adjustment of the camera optics and/or of the image capture area of sensors 166 (FIG. 5). It is an advantage of CMOS image sensors, such as the above-mentioned MV-13, that they allow the number of rows in the image to be adjusted, without necessarily reducing the output pixel rate. In other words, the number of active rows may be reduced or increased to provide a desired image height, so that each die 232 is divided into a fixed, integer number of images 236. The frame rate of the sensor is then increased or reduced to compensate for the change in image height, so as to maintain the desired output pixel rate (and hence the desired throughput of system 20).

Figure 11:
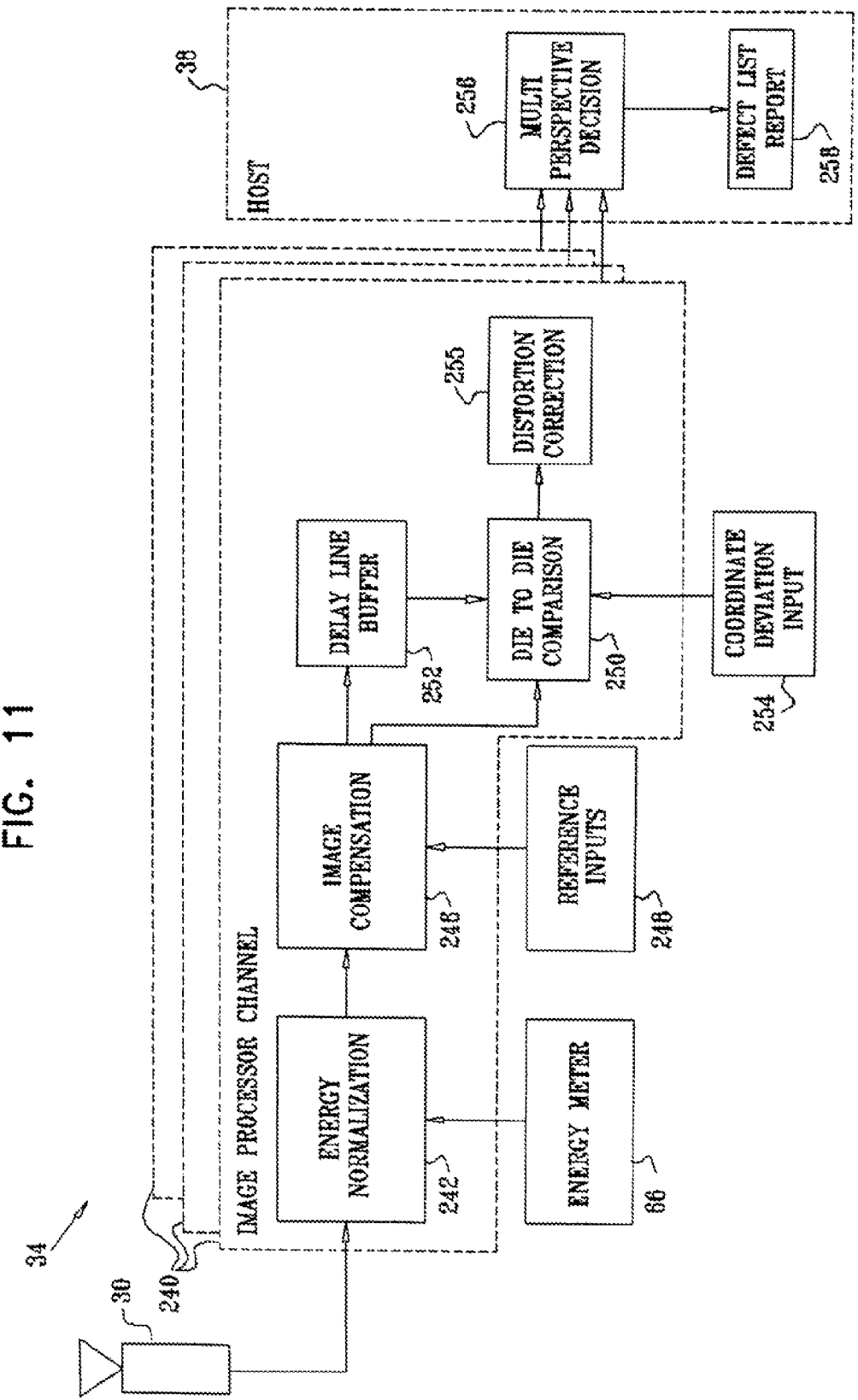
FIG. 11 is a block diagram that schematically illustrates a signal processing subsystem for use in optical inspection, in accordance with an embodiment of the present invention.

FIG. 11 is a block diagram that schematically illustrates signal processing operations performed by image processor 34 and host computer 38, in accordance with an embodiment of the present invention. Image processor 34 comprises multiple processing channels 240, typically one channel for each camera 30. Each image frame captured by camera 30 is transferred to the corresponding channel 240, typically in the form of a sequence of digitized pixel values. Typically, cameras 30 output 8-bit digital values. Sensors 166, such as the above-mentioned CMOS MV-13 sensor, typically comprise on board analog/digital converters, which may output intensity values with higher bit-resolution, such as 10 bits. In this case, each camera 30 may comprise a 10B/8B converter (not shown), which scales the sensor output down to 8-bit values. The scaling may be linear, or it may be chosen so as to emphasize low-intensity features. For this latter purpose, for example, the 10B/8B converter may comprise a look-up table (LUT) with square root or logarithmic scaling from the 10-bit input to the 8-bit output.

In each channel 240, a normalization module 242 corrects the pixel values to compensate for pulse-to-pulse variations in the laser energy, as reported by energy sensors 66 (FIG. 2). An image compensation module 246 then corrects the pixel values for consistent deviations that occur in all the images generated by a given camera, as given by reference inputs 248. The reference inputs are typically pre-calibrated, and reflect variations in the intensity distribution of the laser beam across area 148 that is imaged by the cameras, as well as pixel-to-pixel sensitivity variations and fixed-pattern noise generated by the cameras. The purpose of module 246 is to provide substantially uniform sensitivity over all the pixels in all the images generated by all the cameras.

The pixel value of each pixel in each image frame received from a given camera corresponds to the intensity of light scattered into a certain angle from a particular known location on a known die on wafer 22, depending on the coordinates of stage 36 (FIG. 1). A die-to-die comparison module 250 compares the pixel value for each pixel in the current image frame to the pixel value received by the same camera from the same location in a previously-scanned die. Thus, referring to FIG. 10, each pixel in image a of die B is compared to the corresponding pixel in image a of die A, and so forth. For this purpose, the pixel values recorded in scanning the previous die are held in a delay line buffer 252. Module 250 uses coordinate deviation data 254 to properly register the current and previous dies with one another. The coordinate deviation may arise, for example, from positioning inaccuracy by stage 36 (which will be common to all cameras 30 regardless of viewing angle) or from height variations of the wafer surface relative to the optical focus (causing deviation of the coordinates due to the oblique collection angle, which differs from camera to camera).

As long as there are no defects on a given die, all the pixel values for each pixel in the current frame should be identical, to within a predefined tolerance, to the pixel values of the corresponding pixels in the frame read out of buffer 252. On the other hand, if the value of a given pixel differs from the value of the corresponding pixel in the buffered frame by more than a given threshold, the difference may be indicative of a defect at the location of the pixel. Image processing channel 240 reports any pixels at which such deviations are found in the die-to-die comparison to host computer 38, which then compares the values of the deviant pixels reported by the various channels, as described below.

Before channel 240 reports the deviant values to the host computer, however, a distortion corrector 255 adjusts the pixel values to correct for image distortion and mis-registration among the different cameras and processor channels. This sort of distortion results generally from differences in the angles and optical paths of the different cameras. Correcting the distortion can be a computation-intensive task. Therefore, corrector 255 may be configured to correct distortion only for pixels in the area of suspected defects, such as pixels whose values were found by comparison module 250 in one of channels 240 to deviate from the corresponding pixels in the previous die by more than a predetermined threshold. No further computation is required with respect to pixels for which comparison module 250 found no abnormality in any channel (which should include the vast majority of pixels on wafer 22). The threshold and/or other pixel selection criteria may be set so that no more than a certain percentage of the pixels, say 1%, are submitted to corrector 255.

A multi-perspective decision module 256 (typically a software process) in the host computer combines the distortion-corrected deviant pixel readings from all the different channels 240. Based on the values received from the different channels for a given suspect pixel, module 256 is able to assemble an angular profile of the scattered radiation from the corresponding location on wafer 22. This scattering profile enables module 256 to identify and, generally speaking, to classify the defect that has occurred at this location on the wafer, according to pre-programmed decision rules and thresholds. These rules indicate, for example, whether a set of scattering measurements from a given location are indicative of a particle or a scratch (and the size of the particle or scratch). When the scan of wafer 22 is complete, host 38 issues a defect list report 258, indicating the locations and types of all the defects that have been found.

Alternatively, channels 240 may be configured to correct the coordinate distortion over all image pixels, before die-to-die comparisons or other defect detection processing is performed. In this case, there is no need to align images 236 with dies 232, as in the embodiment described above. Die-to-die comparison for each pixel may then be performed with respect to multiple scattering angles (i.e., radiation captured by multiple cameras 30) simultaneously. U.S. patent application Ser. No. 10/097,442, which is assigned to the assignee of the present patent application, and whose disclosure is incorporated herein by reference, describes a multi-detector defect detection method that may be applied in this case, mutatis mutandis. Alternatively or additionally, channels 240 may be configured so that module 250 compares the current die to a comparable die on another wafer, whose pixel values were recorded previously (wafer-to-wafer comparison).

As noted above, although the embodiments described herein refer specifically to dark-field inspection of wafer 22 in system 20, the principles of the present invention may also be applied in other areas of optical inspection, as well as in other types of illumination and imaging systems. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus for reducing speckle in a beam of laser radiation, comprising:

an optical scanner configured to deflect a portion of the beam by diffraction and to scan an incidence angle of the deflected portion of the beam over a range of angles using an acousto-optic transducer and a drive circuit coupled thereto, wherein the beam is a pulsed beam, and the drive circuit applies a frequency-chirped pulse to the acousto-optic transducer in synchronization with the pulsed beam to diffract a first order of the beam and to scan the deflected portion of the beam on a target plane at an angle that varies over a duration of the laser pulse; and output optics, which are coupled to direct the deflected portion of the beam exiting from the scanner so that the beam irradiates a single area of the target plane over a range of different angles, so as to de-correlate the radiation, the output optics including a lens and a diaphragm at a Fourier plane of the lens to stop an undeflected zero order of the beam from passing.

2. The apparatus according to claim 1, wherein the laser radiation comprises pulses shorter than 1 μs in duration.

3. The apparatus according to claim 2, wherein the optical scanner is adapted to scan the beam with sufficient speed so as to reduce a contrast of speckles formed on the area to no more than about 1%.

4. A method for reducing speckle in a beam of laser radiation, comprising:

optically scanning the beam to deflect a portion of the beam by diffraction and to scan an incidence angle of the deflected portion of the beam over a range of angles using an acousto-optic transducer and a drive circuit coupled thereto, wherein the beam is a pulsed beam, and the drive circuit applies a frequency-chirped pulse to the acousto-optic transducer in synchronization with the pulsed beam to diffract a first order of the beam and to scan the deflected portion of the beam on a target plane at an angle that varies over a duration of the laser pulse; and directing the portion of the beam through output optics including a lens and a diaphragm at a Fourier plane of the lens so that the beam irradiates a single area of the target plane over a range of different angles, so as to de-correlate the radiation, the diaphragm stopping an undeflected zero order of the beam from passing.

5. The method according to claim 4, wherein the laser radiation comprises pulses shorter than 1 μs in duration.

6. The method according to claim 5, wherein the scanning of the beam comprises scanning the beam with sufficient speed so as to reduce a contrast of speckles formed on the area to no more than about 1%.

* * * * *